(12) United States Patent
Kiy et al.

(10) Patent No.: US 6,593,128 B1
(45) Date of Patent: *Jul. 15, 2003

(54) METHOD FOR CULTURING CILIATES

(75) Inventors: Thomas Kiy, Frankfurt (DE); Rüdiger Marquardt, Frankfurt (DE)

(73) Assignee: Nutrinova, Frankfurt am Main (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 1277 days.

(21) Appl. No.: 08/676,971

(22) Filed: Jul. 8, 1996

(30) Foreign Application Priority Data

Jul. 7, 1995 (DE) ......................................... 195 24 307

(51) Int. Cl.⁷ .............................. C12N 1/10; C12N 1/00
(52) U.S. Cl. ..................................... 435/258.1; 435/243
(58) Field of Search ............................... 435/258.1, 243

(56) References Cited

U.S. PATENT DOCUMENTS

| | | |
|---|---|---|
| 4,649,118 A | 3/1987 | Anderson |
| 5,008,197 A  * | 4/1991 | Wergeland et al. .... 435/240.24 |

FOREIGN PATENT DOCUMENTS

| | | |
|---|---|---|
| JP | 56095394 | 1/1981 |
| JP | 57074082 | 10/1982 |
| JP | 08133980 | 5/1996 |

OTHER PUBLICATIONS

Hofmann et al., External factors limiting the multiplication potential of Tetrahymena, J. Cell Sci., 50:407–418, 1981.*
Griffiths, Scaling up of animal cell cultures, in Animal Cell Culture, A Practical Approach, R.I. Freshney, Ed., IRL Press, Oxford, England, Chapter 3, pp. 33–69, 1986.*
Gosselin et al., Improvement of fed batch mass culture for gamma linolenic biosynthesis by Tetrahymena Rostrata (Protozoa), Biotech. Letters, 11:423–426, 1989.*
W. Foissner, *Protozoenfauna*, vol. 4/1: Colpodia (Ciliophora), Gustav Fishcer Verlag, 1993.
Schönefeld et al., J. Protozool., vol. 33, No. 1, p. 22, 1986.
Vogel et al., "Qualitative Assay of Dissolved Amino Acids and Sugars Excreted by *Chlamydomonas reinhardtii* (Chlorophyceae) and *Euglena Gracilis* (Euglenophyceae)", J. Phycol. vol. 14., pp. 403–406, 1978.
Fernandez et al., "Axenic Massive Cultivation of *Entamoeba histolytica* Trophozoites in Spinner Flasks and in a Microfermentor", Arch. of Med. Res., vol. 23, No. 2, pp. 57–58, 1992.
Midler, Jr., et al., "A Model System for Evaluating Shear in the Design of Stirred Fermentors", Biotechnology and Bioengineering, vol. VIII, pp. 71–84, 1966.
Gosselin et al., "Improvement of Fed Batch Mass Culture For γ Linolenic Biosynthesis by Tetrahymena Rostrata (Protozoa)", Biotech. Ltrs., vol. 11, No. 6, pp. 423–426, 1989.
Kiy et al., "Continuous high–cell–density fermentation of the ciliated protozoon Tetraymena in a perfused bioreactor", Appl. Microbiol. Biotechnol., vol. 38, pp. 141–146, 1992.
Munro, "Protozoa as Sources of Commercially Producted Enzymes—A Review", Process Biochemistry, pp. 139–144, 1985.
Ayerbe, "Protozoa *Tetrahymena pyriformis* as single cell protein: fermentation and nutritional aspects", Enzyme Microb. Technol., vol. 2, pp. 54–58, 1980.

* cited by examiner

Primary Examiner—Jon P. Weber
(74) Attorney, Agent, or Firm—Foley & Lardner

(57) ABSTRACT

The invention relates to a method for culturing ciliates comprising the steps of placing ciliates and medium therefor in a culture flask; providing said culture flask with a stirrer having a magnetic core, wherein said stirrer is suspended in the top part of the culture flask such that the stirrer does not touch the flask bottom, and wherein the motion of said stirrer is driven by means of a magnetic field; and stirring said ciliates in said culture medium.

14 Claims, 4 Drawing Sheets

Fig. 1a

Spinner flasks suitable for culturing ciliates

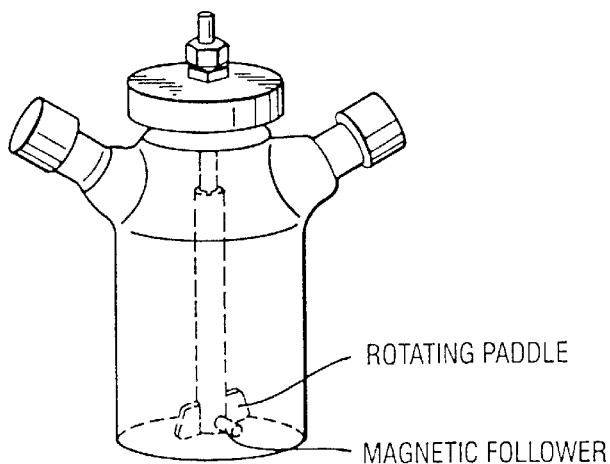

From: R. Ian Freshney, Culture of Animal Cells, 1983, Alan R. Liss, Inc.

Fig. 1b

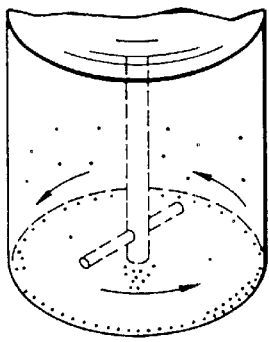

Conventional spinner flask for microcarrier cultures

Fig. 1c

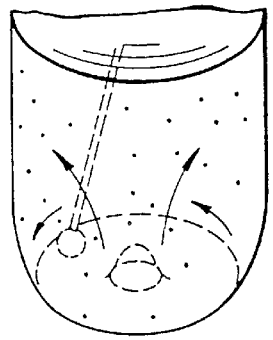

Newly developed culture flask for microcarrier cultures. The arrangement of the spherical magnets in the circular bottom trough makes possible higher cell yields than in conventional spinner vessels.

From: T. Lindl & J. Bauer, [Cell and tissue culture], 1987, Gustav Fischer Verl.

Fig. 2 Superspinner flask suitable for culturing ciliates

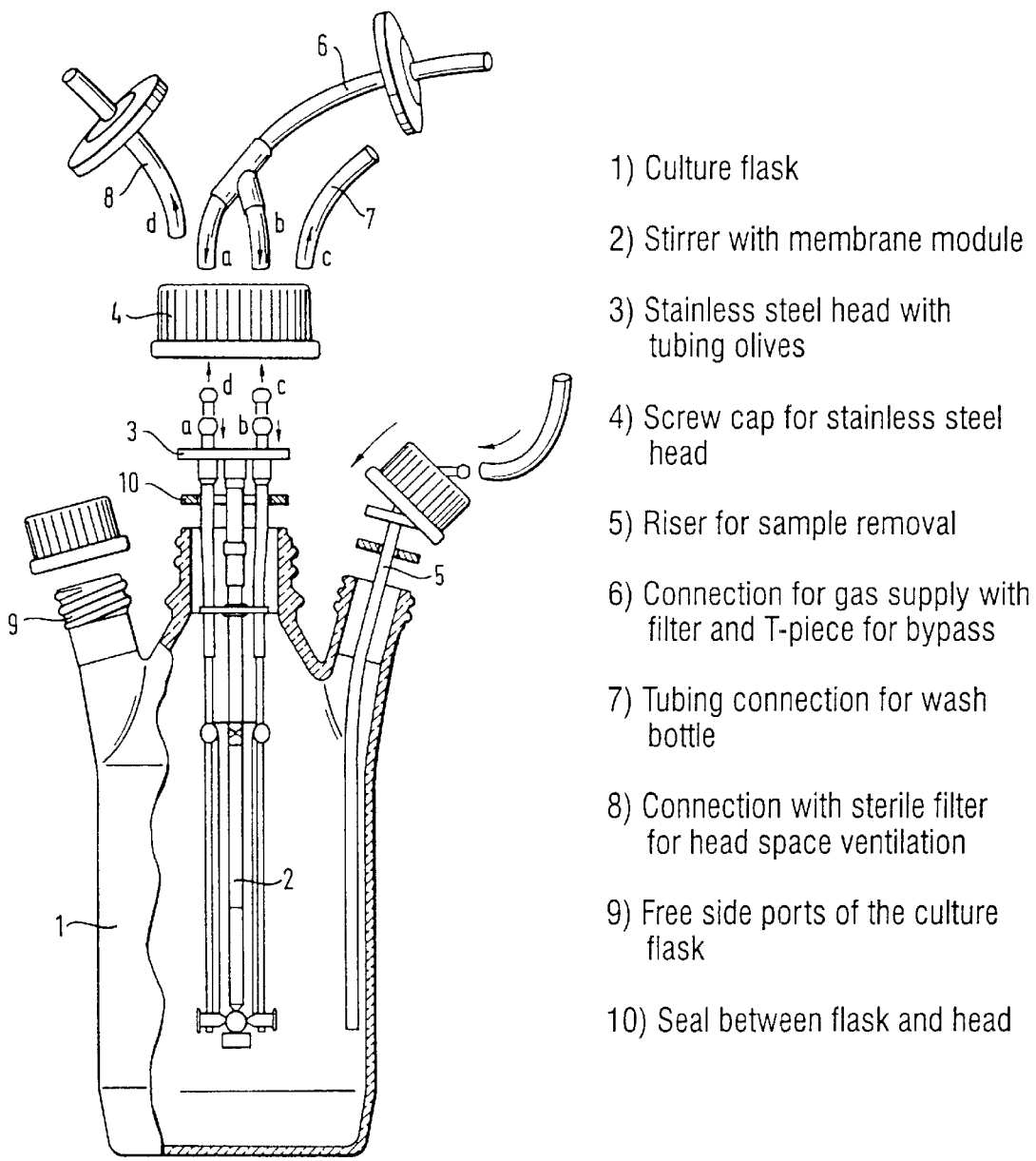

1) Culture flask
2) Stirrer with membrane module
3) Stainless steel head with tubing olives
4) Screw cap for stainless steel head
5) Riser for sample removal
6) Connection for gas supply with filter and T-piece for bypass
7) Tubing connection for wash bottle
8) Connection with sterile filter for head space ventilation
9) Free side ports of the culture flask
10) Seal between flask and head From: Fraune et al.,[CycloBatch cell culture in the SuperSpinner], 1995, BioTec, 2, 16

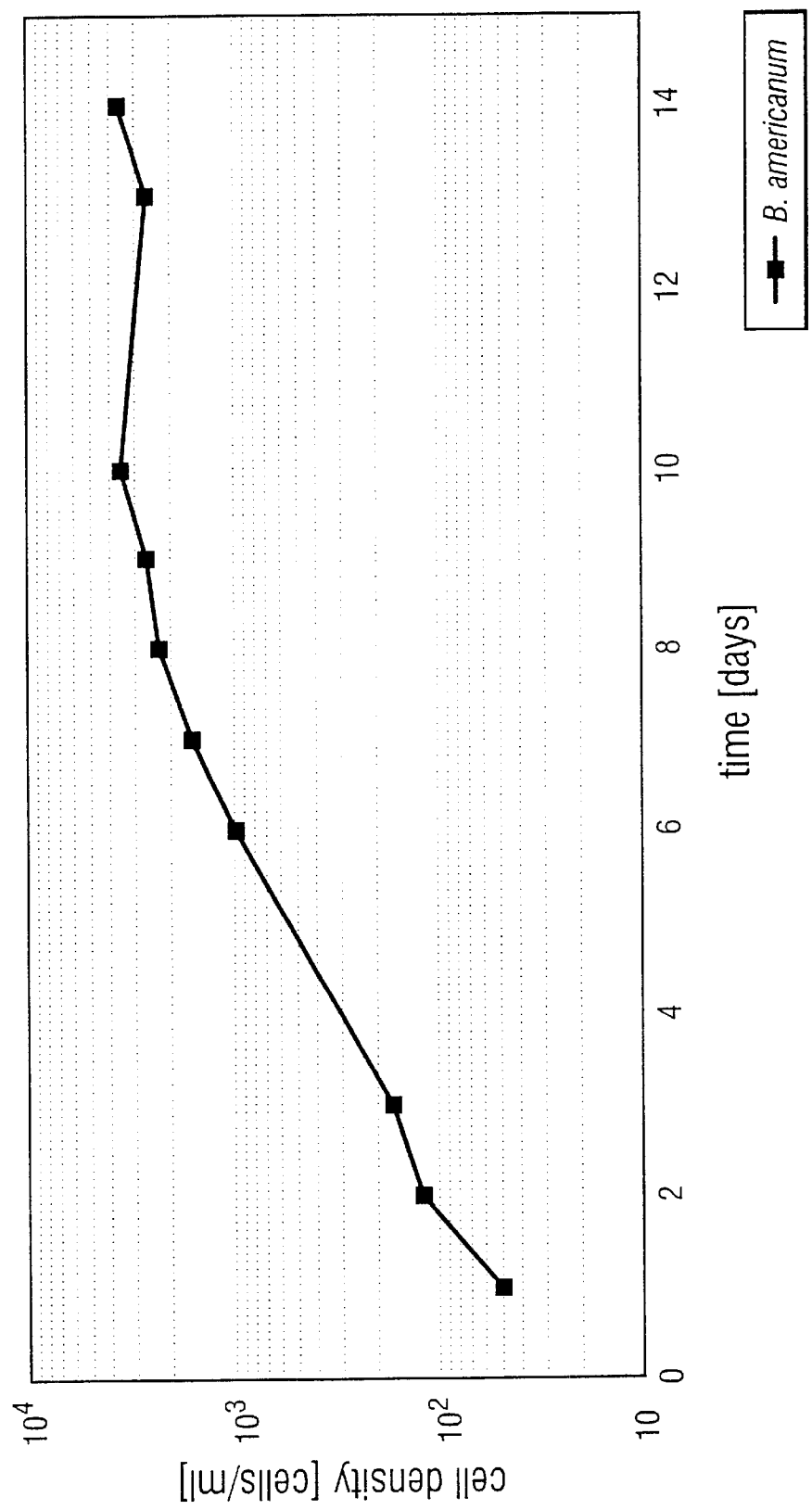
Fig. 3: Growth of *Blepharisma americanum* in spinner flasks

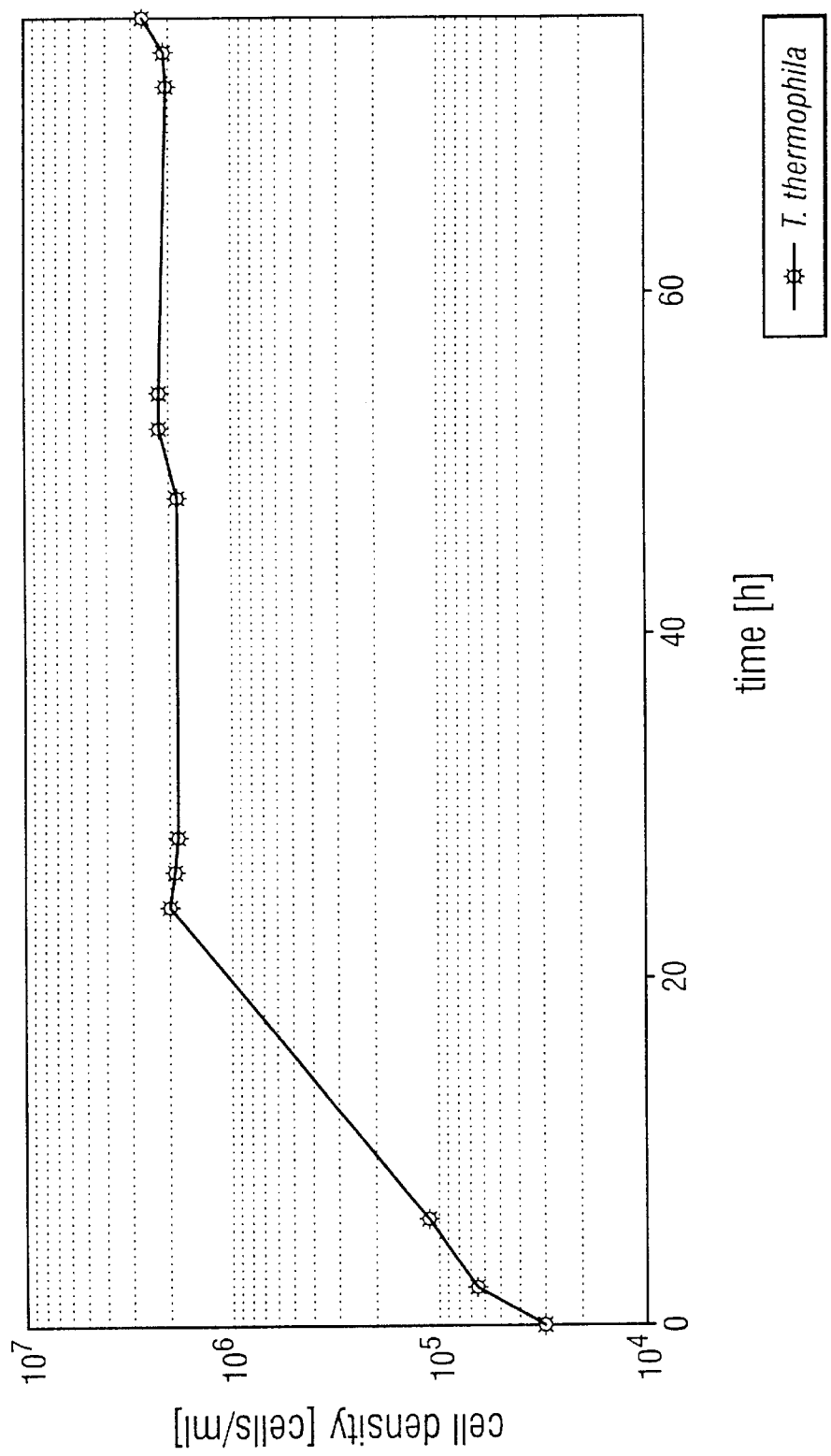
Fig. 4: Growth of Tetrahymena thermophila in spinner flasks

METHOD FOR CULTURING CILIATES

FIELD OF THE INVENTION

The invention relates to a method for culturing ciliates comprising stirring ciliates in culture medium.

BACKGROUND OF THE INVENTION

Ciliates, protozoans belonging to the phylum Ciliophora, are a promising source of useful biogenic materials, such as, for example, enzymes (I. Munro, 1985, *Process Biochem.* 20: 139), unsaturated fatty acids (Y. Gosselin et al., 1989, *Biotechnol. Lett.*, 11: 423) and "single cell protein" (A. Ayerbe, 1980, *Enzyme Microb. Technol.*, 2: 54).

A reason for the fact that ciliates, despite their potential, have not been used industrially as productive organisms until now, lies in the often poor culturability of these organisms. The central problems in the fermentation of ciliates include the lack of suitable, cost-effective culture media and the often high sensitivity to shear forces (Y. Gosselin et al., 1989, *Biotechnol. Lett.*, 11: 423; M. Midler & R. K. Finn, 1966, *Biotechnol. Bioeng.*, 8: 71). While some ciliates such as, for example, Tetrahymena and Paramecium can be cultured successfully in fermenters (T. Kiy & A. Tiedtke, 1992, *Appl. Microbiol. Biotechnol.*, 38: 141; U. Sch önefeld et al., *J. Protozool.*, 33: 222), for the majority of ciliates there is to date no method for mass culturing. However, even the above-mentioned genera cannot be cultured undamaged in conventional fermenters. This can be recognized, inter alia, in that the degree of damage to Tetrahymena cells has been used as a measure of the shear forces in stirred fermenters (M. Midler & R. K. Finn, 1966, *Biotechnol. Bioeng.* 8: 71). Many ciliates were until now propagated only on a very small scale, at very low cell densities. Thus the customary method for the culture of colpodid soil ciliates is still the "flooded petri dish" method, in which a few ml of culture are incubated in Petri dishes (W. Foissner, 1993, *Protozoenfauna:* [*Protozoan fauna*] Vol. 4/1: Colpodia (Ciliophora), Gustav Fischer Verl.).

A method for culturing ciliates in mass cultures would be desirable. Such a system is to be regarded as a prerequisite for the assessment or use of these organisms as a source of useful biogenic materials.

The shear forces occurring in conventional fermenters are not tolerated by many ciliates. A system which produces relatively low shear forces, but nevertheless guarantees adequate mixing of the culture, is the so-called spinner flask (FIG. 1). Typical of this system is the stirrer with magnetic core, driven by a magnetic stirrer located under the culture vessel. The stirrer brings about gentle and low shear-stress mixing.

Although this culturing method had already been developed many years ago (T. Lidl & J. Bauer, 1987, Zell—und Gewebekultur [*Cell and tissue culture*], Gustav-Fischer Verl.), for culturing animal cell cultures (e.g. hybridoma cells), the transfer of this culturing method to free-living ciliates did not occur. Only distantly related eukaryotes such as Euglena from the Euglenophyceae, Chlamydomonas from the Chlorophyceae group (Vogels et al., 1978, *J. Phycol.*, 14, 403) and *Entamoeba histolytica* from the Amoebida group (Said-Fernandez, et al., 1992, Arch. Med. Res., 23, 57) have already been cultured in spinner flasks.

SUMMARY OF THE INVENTION

It is an object of the invention to provide a method for culturing ciliates comprising the steps of placing ciliates and medium therefor in a culture flask; providing said culture flask with a stirrer having a magnetic core, wherein said stirrer is suspended in the top part of the culture flask such that the stirrer does not touch the flask bottom, and wherein the motion of said stirrer is driven by means of a magnetic field; and stirring said ciliates in said culture medium. It is a further object of the invention to provide a culturing method comprising stirring ciliates in culture medium, wherein the stirrer is a membrane aeration stirrer.

It is another object of the invention to provide a culturing method comprising stirring ciliates in culture medium, wherein the culturing comprises batch fermentation, fed-batch fermentation, or cyclic medium exchange.

It is a further object of the invention to provide a culturing method comprising stirring ciliates in culture medium, wherein the stirring speed is from about 1 to about 70 rpm. It is also an object of the invention to provide such a method wherein the stirring speed is from 1 to 70 rpm.

It is yet a further object of the invention to provide a culturing method comprising stirring ciliates in culture medium, wherein the stirring speed is from about 10 to about 40 rpm. It is also an object of the invention to provide such a method wherein the stirring speed is from 10 to 40 rpm.

It is yet a further object of the invention to provide a culturing method comprising stirring ciliates in culture medium, wherein the stirring mode is a reciprocatory mixing technique.

It is yet a further object of the invention to provide a method for culturing ciliates, wherein such a method comprises any combination of the foregoing objects.

Finally, it is an object of the invention to provide a method for culturing ciliates, comprising any combination of the foregoing objects, wherein the ciliates belong to the group Colpodia, Holotrichia, Peritrichia, Spirotrichia or Suctoria.

BRIEF DESCRIPTION OF THE DRAWINGS

FIG. 1 shows spinner flasks that are suitable for culturing ciliates. FIG. 1A shows a spinner flask with a rotating paddle and a magnetic follower. See Freshney, R. *Culture of Animal Cells* 237 (Alan R. Liss: 1983). FIG. 1B shows a conventional spinner flask for microcarrier cultures. FIG. 1C shows a newly developed culture flask for microcarrier cultures. The arrangement of the spherical magnets in the circular bottom trough makes possible higher cell yields than in conventional spinner vessels. See Lindl, et al. *Cell and Tissue Culture* 125 (Gustav Fischer Verl: 1987).

FIG. 2 shows a superspinner flask suitable for culturing ciliates.

FIG. 3 shows the growth of *Blepharisma americanum* in spinner flasks. Cell density (cells/ml) is plotted against culturing time in days (d).

FIG. 4 shows growth of *Tetrahymena thermophila* in spinner flasks. Cell density (cells/ml) is plotted against culturing time in hours (h).

DETAILED DESCRIPTION OF THE INVENTION

Surprisingly, it has been found that spinner flask culturing can be applied to ciliates. Thus, the present invention relates to a method for culturing ciliates with stirring of the culture medium, which is distinguished in that, as a culture vessel, a culture flask is used which has a stirrer provided with a magnetic core which is suspended in the top part of the culture flask such that the stirrer does not touch the flask bottom, the stirrer being driven by means of a magnetic field, such as a so-called "spinner flask." As used in this specification, a "culture" flask means any vessel or container that is capable of containing liquid culture medium and is adapted to contain a stirrer provided with a magnetic core. A culture flask according to the invention includes, but is not limited to, a spinner flask and a superspinner flask. Using a method according to the present invention, the following ciliates were successfully cultured in spinner flasks: representatives of the groups Colpodia (e.g. Colpoda, Platyophrya), the Holotrichia (e.g. Tetrahymena, Paramecium, Colpidium), the Peritrichia (e.g. Vorticella) and the Spirotrichia (e.g. Blepharisma, Stentor, Euplotes, Stylonichia). Nomenclature according to K. Hausmann, 1985, Protozoologie [Protozoology], Georg Thieme Verl. Any other type of ciliate can be cultured using the methods of the present invention, such as Suctoria.

The growing temperature for ciliates cultured according to the methods of the invention can be between 10° and 40° or 13° and 35°, and other acceptable ranges are between 20° and 38°, and 20° and 30° C. The growing temperature for ciliates cultured according to the methods of the invention can also be from about 10° to about 40° or about 13° C. to about 35° C., and other acceptable ranges are from about 20° C. to about 30° C. and from about 20° to about 38°.

The ciliates can be grown in axenic media, which is media free from other living organisms (for example, Tetrahymena can be grown in Proteose peptone/yeast extract/Sequestrene (PPYS) medium or skim milk medium). The ciliates can also be grown in media containing one other organism (for example, Blepharisma can be grown with *Bacillus subtilis* or *Pseudomonas fluorescens* as a feed bacterium), or in media containing more than one other organism.

The culturing can be carried out as a batch fermentation (where organisms are grown in culture vessels without additional feeding after inoculation), fed-batch fermentation (regular feeding of a substrate) or fermentation with cyclic medium exchange.

Beside the spinner flasks (FIG. 1), superspinner flasks (FIG. 2) which comprise a membrane aeration stirrer for the bubble-free aeration of the medium are suitable for culturing ciliates. A membrane aeration stirrer is also known as an open pore hydrophobic membrane and consists of a moving clew or basket consisting of membrane tubes. Such stirrers provide oxygen to cells in culture flasks and maintain culture medium homogeneity without the formation of bubbles. The stirrer tubes can be made with a hydrophobic material such as polypropylene having a porous asymmetric structure. Oxygen gas is fed through the tubes. See BioTec 2:16 (1995) and Gesellschaft fur Biotechnologishe Forschung mbH Braunschweig (GBF) Product Circular: "Bubble-free tissue culture aeration.", both of which are incorporated herein in their entireties by reference. Superspinner flasks have only been employed until now for the production of monoclonal antibodies from hybridoma cells.

The stirring mode can be designed either as a mixing technique with continuous rotation of the spinner in the same direction, or as a reciprocating mixing technique with periodic changes in the direction of rotation of the spinner. The stirrer speed can be between 1 and 70 rpm, and one acceptable or preferred range is 10–40 rpm (rpm=revolutions per minute). The stirrer speed can also be between about 1 and about 70 rpm, and one acceptable or preferred range is from about 10 to about 40 rpm (rpm=revolutions per minute).

The following examples are provided to illustrate the present invention, and in no way limit the scope of the present invention.

EXAMPLES (All species are available either via the American Culture Collection, Rockville, Md., USA or the Culture Collection of Algae and Protozoa, Ambleside, Cumbria, United Kingdom).

1. *Blepharisma americanum* was incubated at 25° C. in a 2 l TECNOMARA® cell spinner vessel in 1 l of standard medium (9 parts of Volvic water, 1 part of lettuce medium, a few autoclaved wheat grains). The stirrer speed was 30 rpm. After 14 days, the cells had achieved a density of 3600 cells/ml (FIG. 3). By repeated feeding (1 time per week) of a bacterial suspension (10 ml/500 ml, first added to medium at 7 days; strain 12658 from the American Type Culture Collection), cell densities of 50,000 cells/ml were achieved after 21 days. The inoculation density was 50 cells/ml.

2. *Colpoda cucullus* was incubated at 25° C. in a 1 l TECNOMARA® cell spinner vessel in 500 ml of standard medium (9 parts of Volvic water, 1 part of lettuce medium, a few autoclaved wheat grains). 10 ml of an autoclaved bacterial suspension (strain 12658 from the American Type Culture Collection) were additionally fed. The stirrer speed was 30 rpm; the inoculation density 100 cells/ml. Cell densities of 10,000 cells/ml were determined after 280 h.

3. *Colpoda steinii* was incubated at 25° C. in a 1 l TECNOMARA® cell spinner vessel in 500 ml of S/W medium (CCAP catalog, 1988, Titus Wilson & Son Ltd., Kendal). The stirrer speed was 30 rpm; the inoculation density 50,000 cells/ml. Cell densities of $10^7$ cells/ml were determined after 48 hours.

4. *Platyophrya macrostoma* was incubated at 25° C. in a 2 l TECNOMARA® cell spinner vessel in 700 ml of medium (9 parts of Volvic water, 1 part of lettuce medium) with addition of 10 ml of autoclaved 10% strength yeast suspension. The stirrer speed was 30 rpm. After 150 h, the cells achieved a concentration of 70,000 cells/ml. The inoculation density was $10^4$ cells/ml.

5. *Tetrahymena thermophila* was cultured at 25° C. in a 1 l TECNOMARA® cell spinner vessel in 500 ml of skim milk medium (2% skim milk powder, 0.5% yeast extracts, 0.1% glucose, 0.003% Sequestrene). Mixing was carried out by means of the reciprocating mixing technique with periodic changes in the direction of rotation (30 rpm). After 24 h, the cells had achieved a cell density of $2\times10^6$ cells/ml (FIG. 4). The inoculation density was $3\times10^4$ cells/ml.

6. *Tetrahymena setosa* was cultured at 25° C. in a 1 l TECNOMAPA® cell spinner vessel in 500 ml of skim milk medium (2% Pharmamedia, 0.5% yeast extract, 0.1% glucose, 0.003% Sequestrene). Mixing was carried out by means of the reciprocating mixing technique with a periodic changes in the direction of rotation (30 rpm). After 24 h, the cells had achieved a cell density of $3\times10^6$ cells/ml. The inoculation density was $3\times10^4$ cells/ml.

7. *Colpidium campylum* was cultured at 25° C. in a 1 l TECNOMARA® cell spinner vessel in 500 ml of skim milk medium (2% skim milk powder, 0.5% yeast extracts, 0.1% glucose, 0.003% Sequestrene). Mixing was carried out by means of the reciprocating mixing technique with a change in the direction of rotation (30 rpm). After 72 h, the cells had achieved a cell density of $1.2\times10^6$ cells/ml. The inoculation density was $2.2\times10^4$ cells/ml.

It will be apparent to those skilled in the art that various modifications and variations can be made to the compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually.

This application incorporates by reference, in total, the entire specification, claims, drawings and abstract of priority application German Patent Application No. 195 24 307.2, filed Jul. 7, 1995.

We claim:

1. A method for culturing ciliates, comprising the steps of:

placing ciliates and medium therefor in a culture flask;

providing said culture flask with a stirrer having a magnetic core, wherein said stirrer is suspended in the top part of the culture flask such that the stirrer does not touch the flask bottom, and wherein the motion of said stirrer is driven by means of a magnetic field; and stirring said ciliates in said culture medium.

2. The method as claimed in claim 1, wherein the stirrer is a membrane aeration stirrer.

3. The method as claimed in claim 1, wherein the culturing comprises fed-batch fermentation.

4. The method as claimed in claim 1, wherein the culturing comprises cyclic medium exchange.

5. The method as claimed in claim 1, wherein the stirring speed is from about 1 to about 70 rpm.

6. The method as claimed in claim 5, wherein the stirring speed is from about 10 to about 40 rpm.

7. The method as claimed in claim 1, wherein the stirring speed is from 1 to 70 rpm.

8. The method as claimed in claim 7, wherein the stirring speed is from 10 to 40 rpm.

9. The method as claimed in claim 1, wherein the stirring is a reciprocating mixing technique.

10. The method as claimed in claims 1, wherein the ciliates belong to the Colpodia group.

11. The method as claimed in claim 1, wherein the ciliates belong to the Holotrichia group.

12. The method as claimed in claims 1, wherein the ciliates belong to the Peritrichia group.

13. The method as claimed in claim 1, wherein the ciliates belong to the Spirotrichia group.

14. The method as claimed in claim 1, wherein the ciliates belong to the Suctoria group.

* * * * *